United States Patent [19]

Mallebrein et al.

[11] Patent Number: 5,255,554
[45] Date of Patent: Oct. 26, 1993

[54] CONNECTING CIRCUIT FOR AN OXYGEN PROBE AND METHOD FOR CHECKING FOR A CORRECT PROBE CONNECTION

[75] Inventors: Georg Mallebrein; Helmut Denz, both of Stuttgart, Fed. Rep. of Germany

[73] Assignee: Robert Bosch GmbH, Stuttgart, Fed. Rep. of Germany

[21] Appl. No.: 977,028

[22] Filed: Nov. 16, 1992

[30] Foreign Application Priority Data

Nov. 15, 1991 [DE] Fed. Rep. of Germany ....... 4137626

[51] Int. Cl.⁵ ............... G01N 31/00; G01N 27/416; F02D 41/14; F02D 41/22
[52] U.S. Cl. .................... 73/23.32; 123/690
[58] Field of Search ............... 123/688, 690, 691, 696; 73/23.32, 116, 117.3, 118.1

[56] References Cited

U.S. PATENT DOCUMENTS

| | | |
|---|---|---|
| 3,962,866 | 6/1976 | Neidhard et al. |
| 4,112,893 | 9/1978 | Anzai ........................ 73/23.32 |
| 4,121,548 | 10/1978 | Hattori et al. ............... 73/23.32 |
| 4,258,563 | 3/1981 | Yasuda et al. ............... 73/23.32 |
| 4,306,444 | 12/1981 | Hattori et al. ............... 73/23.32 |
| 4,344,317 | 8/1982 | Hattori et al. ............... 73/23.32 |
| 4,393,841 | 7/1983 | Drews et al. ............... 73/23.32 |
| 4,622,809 | 11/1986 | Abthoff et al. |
| 4,742,808 | 5/1988 | Blümel et al. ............... 73/23.32 |
| 4,771,755 | 9/1988 | Asakura et al. ............... 123/690 |
| 4,796,587 | 1/1989 | Nakajima et al. ............... 73/23.32 |
| 4,803,866 | 2/1989 | Miki et al. ............... 73/23.32 |
| 4,932,238 | 6/1990 | Yoshida et al. ............... 73/116 |

FOREIGN PATENT DOCUMENTS

03-272452 12/1991 Japan ................... 73/23.32

Primary Examiner—Willis R. Wolfe
Assistant Examiner—Thomas Moulis
Attorney, Agent, or Firm—Walter Ottesen

[57] ABSTRACT

The invention relates to a connecting circuit for a potential-free oxygen probe having a low-potential line and a high-potential line and includes: an amplifier; an offset voltage source connected to the high-potential line forward of the amplifier for applying an offset potential to the high-potential line; the amplifier having an input connected across the high-potential and low-potential lines to receive the difference between the potentials on the lines as an input voltage; the amplifier being adapted to amplify the input voltage and having an output for supplying an output voltage equal to the difference between the offset voltage and the amplified input voltage; and, the offset voltage being selected so as to cause the output voltage to always be greater than zero but less than a pregiven threshold voltage. This connecting circuit makes it possible to determine faults for probe connections, for example, short circuits of the line to ground. The output voltage then drops to 0 V which is not possible for proper operation in view of the offset voltage used. The threshold voltage is exceeded for shorts to battery potential. A method for checking for a correct probe connection is also disclosed.

9 Claims, 4 Drawing Sheets $$\text{UIN\_V} = \text{Uo} + (\text{Ro}/(\text{Ro} + \text{RS\_V})/(\text{US\_V} - \text{Uo}) \quad (1)$$

$$\text{UOUT\_V} = \text{Up} - v \times \text{UIN\_V} \quad (2)$$

$$\text{Up} < \text{U\_REF} - v \times |\text{U\_MIN}| - \Delta \text{U} \quad (3)$$

$$\text{Up} > v \times |\text{U\_MAX}| + \Delta \text{U} \quad (4)$$

$UIN\_V = Uo + (Ro/(Ro + RS\_V)/(US\_V - Uo)$ (1)
$UOUT\_V = Up - v \times UIN\_V$ (2)
$Up < U\_REF - v \times |U\_MIN| - \Delta U$ (3)
$Up > v \times |U\_MAX| + \Delta U$ (4)

$UOUT\_H = Up - v \times UIN\_H = Up - v \times US\_H$ (5)

CONNECTING CIRCUIT FOR AN OXYGEN PROBE AND METHOD FOR CHECKING FOR A CORRECT PROBE CONNECTION

FIELD OF THE INVENTION

The invention relates to a connecting circuit for a potential-free oxygen probe as well as a method for checking whether the oxygen probe is correctly connected or if short circuits and/or interruptions are present in the lines.

BACKGROUND OF THE INVENTION

Oxygen probes will be referred to in the following as simply probes for brevity. That line of the two connecting lines of such probes which normally carries a higher potential than the other line is referred to in the following as a high-potential line whereas the other line is referred to as a low-potential line.

Probes and especially those of the Nernst type exhibit from probe to probe a relatively wide distribution in the voltages which in each case are emitted for a specific air ratio, for example, for the exhaust gas of a motor vehicle. This makes checking for the correct connection of such a probe difficult because a voltage for the one probe is still plausible which, for another probe, would already clearly indicate a fault. Typically, the probe voltage of a Nernst probe lies between 850 mV for measuring a rich mixture and at approximately 100 mV for measuring a lean mixture. However, a first probe can indicate, for example, almost 1 V when measuring a rich mixture and another can measure approximately −80 mV when measuring a lean mixture. 0 V are measured if a short circuit is present between the two wires of a two-wire pair. For the second-mentioned probe, this is a plausible measurement value since even negative voltages can occur which are, however, not evaluated by the typical evaluation circuits; instead, the negative voltages are made equal with a voltage of 0 V. Plausible voltages also occur, for example, when a probe line has become separated from a control apparatus.

In order to reliably determine two-wire short circuits or line separations, the conventional procedure has been that, when the probe voltage has exhibited the value 0 V or the voltage of an ancillary voltage source over a pregiven time span, then the air/fuel mixture is arbitrarily slightly enriched. If the probe signal does not respond to this enrichment, then this is a reliable indication that a fault is present. It is a disadvantage of this test method that the mixture must be enriched which leads to an increased exhaust-gas discharge and also causes other disadvantages.

Oxygen probes are mostly so arranged that they determine the gas composition in the exhaust-gas flow forward of a catalytic converter. However, it is also known from U.S. Pat. Nos. 3,962,866 and 4,622,809 to provide an additional probe rearward of a catalytic converter in order to monitor the converting capacity of the catalytic converter with the aid of this probe. As long as the catalytic converter provides excellent conversion, a gas mixture of a very uniform composition flows past the rearward probe during steady-state operation of the corresponding internal combustion engine. Then, a voltage which is essentially constant is continuously measured. This fact leads to difficulties in checking the operability of the probe rearward of the catalytic converter since, for a probe voltage which remains continuously constant, it is unclear whether the probe is no longer correctly connected or whether the conversion of the catalytic converter is so good that no changes occur. A check is however possible even in this case in that a mixture is arbitrarily generated over a longer time which deviates from the air ratio one. This leads to the condition that a rich or lean mixture also occurs at the output of the catalytic converter. This causes the above-mentioned disadvantages.

SUMMARY OF THE INVENTION

In view of the above, it is an object of the invention to provide a connecting circuit for a probe which is so configured that the circuit makes it possible to determine faults in the connection of the probe without the necessity of arbitrarily changing the mixture composition. It is another object of the invention to provide a method for achieving this purpose.

The above objects are realized with a circuit and method which are the subject matter of copending U.S. patent application Ser. No. 872,810, filed Apr. 24, 1992. The circuit is known in the meantime from the distribution of data sheets. The circuit is so configured that the low-potential line is set to an increased potential with the aid of an offset voltage source. This makes possible a method wherein a check can be made as to whether a probe voltage is measured which is less than the offset voltage.

The connecting circuit of the invention is for a potential-free oxygen probe having a low-potential line and a high-potential line. The connecting circuit includes: an amplifier; an offset voltage source connected to the high-potential line forward of the amplifier for applying an offset potential to the high-potential line; the amplifier having an input connected across the high-potential and low-potential lines to receive the difference between the potentials on the lines as an input voltage; the amplifier being adapted to amplify the input voltage and having an output for supplying an output voltage equal to the difference between the offset voltage and the amplified input voltage; and, the offset voltage being selected so as to cause the output voltage to always be greater than zero but less than a pregiven threshold voltage.

The threshold voltage is preferably equal to the reference voltage of an analog/digital converter. The offset voltage must then be less than the reference voltage plus the amount of the amplified smallest possible (negative) probe voltage.

The method of the invention is for checking the correct connection of a potential-free oxygen probe having a low-potential line and a high-potential line. The method includes the steps of: raising the potential on the high-potential line relative to ground by a pregiven offset voltage; applying the difference of the potentials on the lines to an amplifier as an input voltage; amplifying the input voltage and subtracting the amplified input voltage from the offset voltage to form a difference voltage as the output voltage of the amplifier; deeming the probe to be improperly connected when the output voltage is at most zero or corresponds at least to a pregiven threshold voltage; and, selecting the offset voltage so as to cause the output voltage to be always greater than zero and less than the pregiven threshold voltage when the oxygen probe is correctly connected.

It is advantageous to connect the low-potential line to the threshold voltage via a pull-up resistor in order to be able to determine not only ground shorts with the aid of the offset voltage but also, for example, interruptions. In the case of an interruption, at least this threshold voltage is then emitted which, as mentioned above, is greater than the highest possible output voltage for a probe which is correctly connected.

Advantageously, the above-mentioned output voltage is converted by an analog/digital converter into a digital value for further evaluation. In this case, the threshold value is set equal to the reference voltage of the analog/digital converter.

BRIEF DESCRIPTION OF THE DRAWINGS

The invention will now be described with reference to the drawings wherein.

DESCRIPTION OF THE PREFERRED EMBODIMENTS OF THE INVENTION

In the following, reference is often made to resistors and voltage sources. For this purpose, the designations of these components correspond to the resistor values or voltage values. For example, Up identifies an offset voltage source as a component as well as the voltage of this voltage source. RS_V is correspondingly the designation for a resistor component as well as for the resistance value of this component. Here, RS_V is the equivalent resistance of a probe forward of a catalytic converter.

Figure 1:
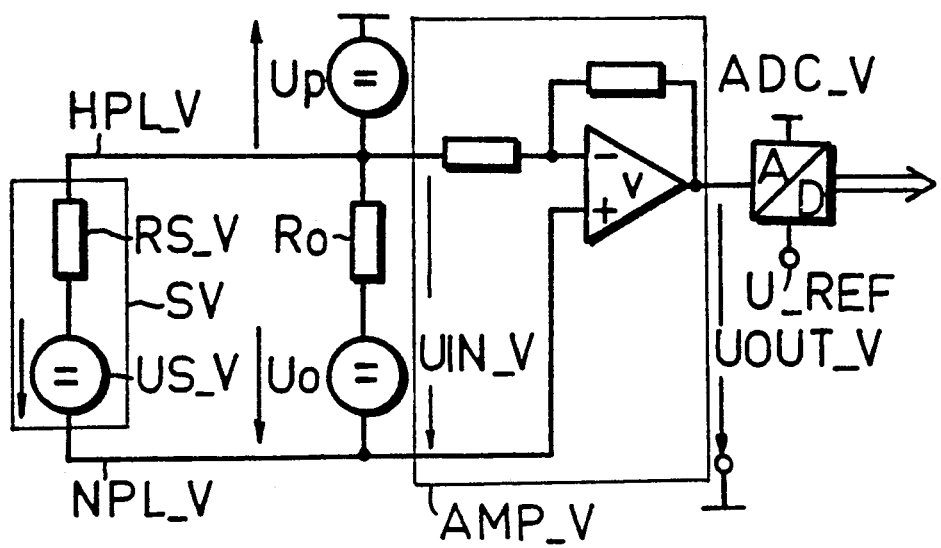
FIG. 1 is a schematic circuit diagram of a probe-connecting circuit having ancillary and offset voltage sources.
Figure 2:
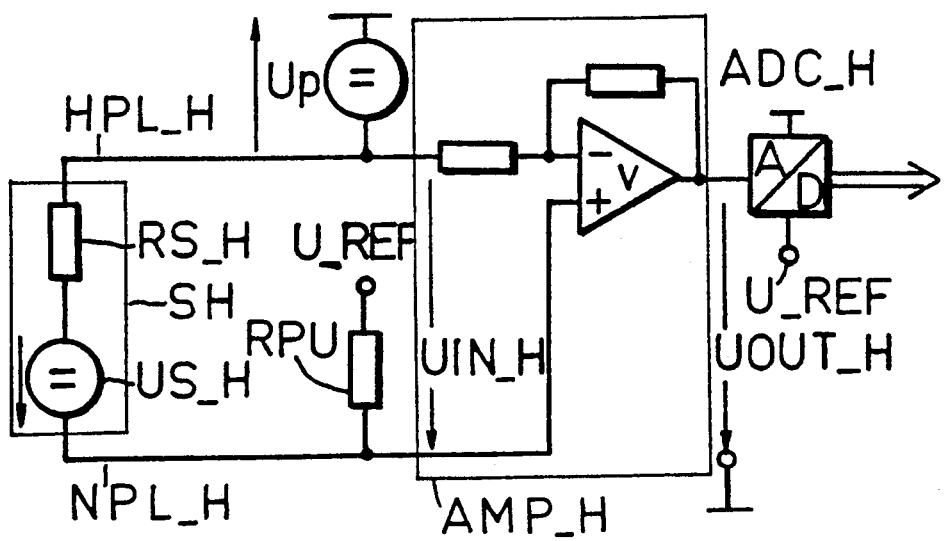
FIG. 2 is a schematic circuit diagram of a probe-connecting circuit having an offset voltage source and a pull-up resistor.
Figure 3:
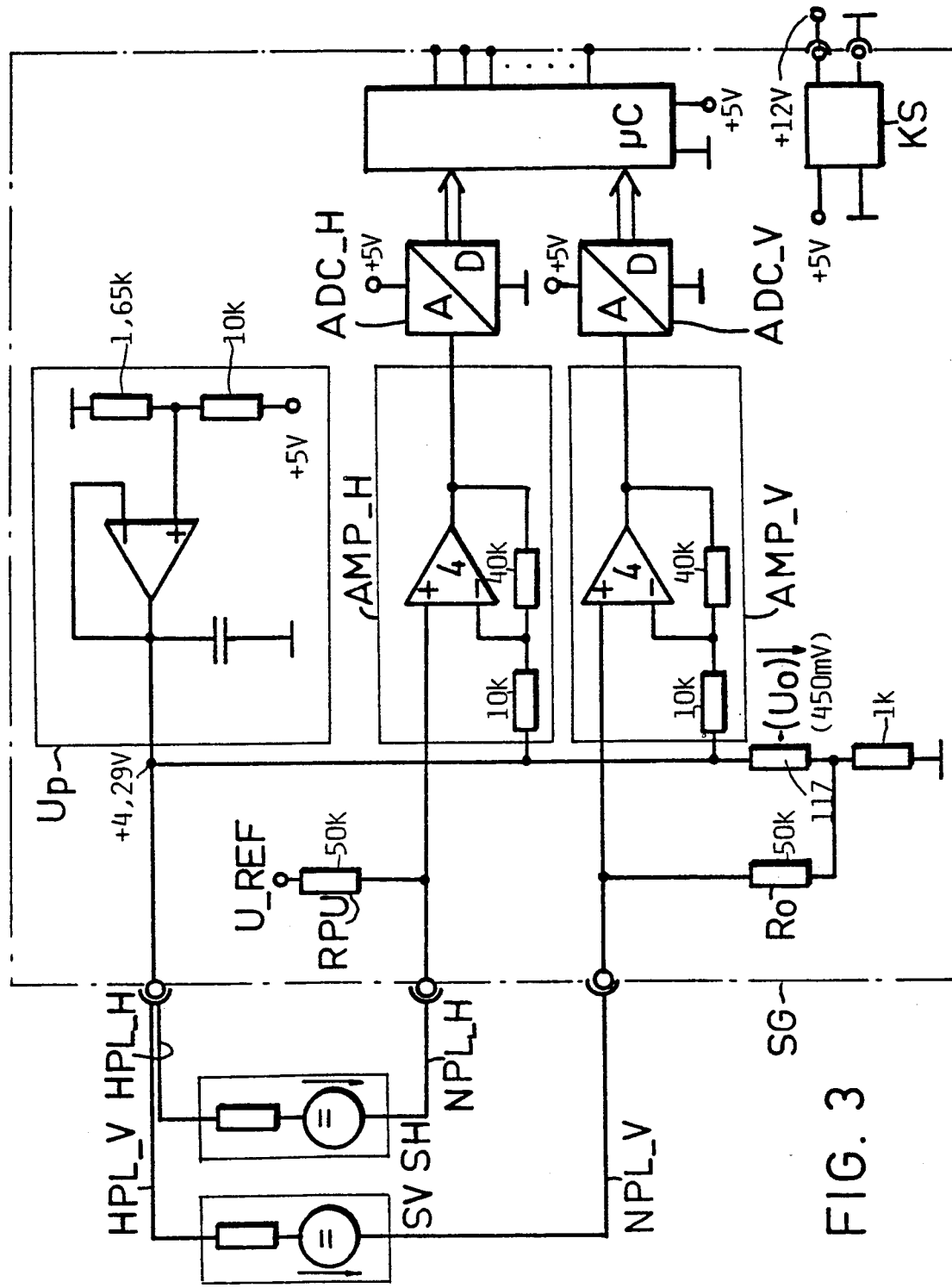
FIG. 3 is a circuit diagram of a connecting circuit for two probes having a common offset voltage source.

Before FIGS. 1 and 2 are discussed in detail, a prefatory overview will be provided with respect to FIG. 3.

FIG. 3 shows a control apparatus SG to which a probe SV is connected via a high-potential line HPL_V and a low-potential line NPL_V and to which a probe SH is connected via a high-potential line HPL_H and a low-potential line NPL_H. The probe SV is arranged forward of a catalytic converter (not shown) and the probe SH is arranged rearward of the catalytic converter. The two high-potential lines lead to the same terminal of the control apparatus. The offset voltage source Up mentioned above is connected internally to this terminal of the control apparatus. With the aid of this voltage source, both high-potential lines are raised to the potential Up with respect to the ground of the control apparatus. The first and second probe signals are supplied to a microprocessor μC within the control apparatus SG. After inversion, the first probe signal is amplified and a difference is formed with respect to the offset voltage in an amplifier AMP_V and is transmitted to the microprocessor via an analog/digital converter ADC_V. The second signal is amplified and a difference voltage is formed with respect to the offset voltage in an amplifier AMP_H and is supplied to the microprocessor via an analog/digital converter ADC_H. The analog/digital converters limit the values of their input signals to the range between 0 V and a reference voltage. A constant voltage source KS is present in the control apparatus SG for supplying a reference voltage of +5 V. All components shown in FIG. 3 (with the exception of the constant voltage source KS and the microprocessor μC) form the common connecting circuit for the forward probe SV and the rearward probe SH.

FIG. 1 shows the circuit diagram for the forward probe SV while FIG. 2 shows the circuit diagram for the rearward probe SH.

In the circuit of FIG. 1, the high-potential line HPL_V and the low-potential line NPL_V of a forward probe SV are connected to an amplifier AMP_V having an amplification factor (v). The amplifier AMP_V amplifies the inverted probe voltage. The potential of the high-potential line HPL_V is raised with the aid of the offset voltage source Up to the positive potential Up relative to the ground of the control apparatus. The forward probe SV has an equivalent circuit diagram with an equivalent circuit voltage source US_V and an equivalent resistance RS_V. A series circuit including a resistor Ro and a voltage source Uo is connected in parallel to the forward probe. The voltage Uo generated by the voltage source Uo is a voltage which is then emitted by a probe when this probe measures exhaust gas having a mixture with the air number (lambda value) one. The voltage as it is present from this circuit in advance of amplification and before addition of the offset voltage Up is given by equation (1) of FIG. 1. The output voltage UOUT_V for the forward probe is given by equation (2) of FIG. 1.

The output voltage UOUT_V is supplied to an analog/digital converter ADC_V which limits the voltages to the range between 0 V and a reference voltage U_REF and supplies digital values corresponding thereto to the microprocessor. It should be noted that the analog/digital converter can also be part of the microprocessor.

In the circuit of FIG. 2, the high-potential lines HPL_H and the low-potential lines NPL_H of a rearward probe SH are connected to an amplifier AMP_H having the amplification factor (v) with the amplifier amplifying the inverted probe voltage. The low-potential line is connected via a pull-up resistor RPU to the reference voltage. The potential of the high-potential line is raised with the aid of the above-mentioned offset voltage source Up to the positive potential Up relative to the ground of the control apparatus. The output voltage UOUT_H results then from equation (5) of FIG. 2. This voltage is supplied to an analog/digital converter ADC_H. For the range of the digital values of this converter, the same applies as was explained for the value range of the converter ADC_V in the circuit of FIG. 1.

The offset voltage Up in the circuits of FIGS. 1 to 3 is selected in the value range pregiven by the equations (3) and (4) in FIG. 1. This offset voltage must be greater than the maximum probe voltage after amplification so that a defective probe connection can be reliably determined. Compared to this maximum value, a safety margin ΔU is provided. On the other hand, this offset voltage must be less than the reference voltage reduced by the amplified amount of the maximum value of a possible negative probe voltage. Here too, a safety margin ΔU is maintained. In the equations (3) and (4), the amounts of the minimum and maximum probe voltage are identified by |U_MIN| and |U_MAX|, respectively.

The amplifier factor (v) will be pregiven, for example, at (4) when using a conventional analog/digital converter having a reference voltage of 5 V, a maximum occurring probe voltage U_MAX of 1 V and a minimum occurring probe voltage U_MIN of −80 mV. An offset voltage Up of 4.5 V is selected. The amplification factor can be 1 when using an analog/digital converter having a reference voltage of, for example, 1.25 V. The offset voltage Up is then pregiven, for example, with 1.05 V.

The specific design values for resistors shown in FIG. 3 are so selected that: inverting amplifiers AMP_V and AMP_H have the above-mentioned value (4) for the amplification factor, the voltage source Uo generates a voltage of 450 mV and the offset voltage amounts to 4.29 V.

Figure 4:
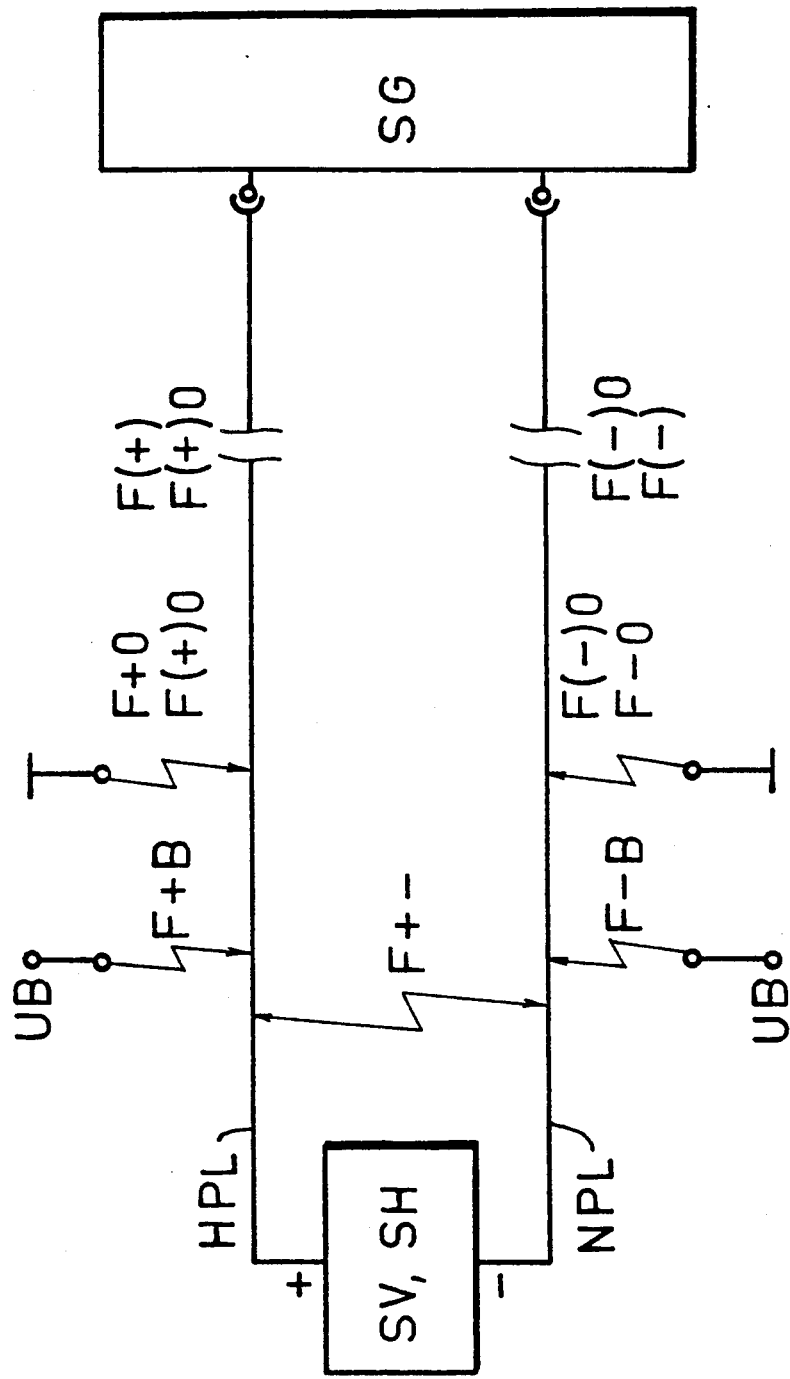
FIG. 4 is a schematic representation for explaining faults in the connection of a probe; and, FIG. 5 is a flowchart for explaining the test method of the invention for determining whether a probe is connected in a defective manner.

FIG. 4 shows nine faults as they can occur at the forward probe SV and/or at the rearward probe SH. Accordingly, a total of 18 individual faults are thereby possible. The faults F+B and F−B are short circuits of the high-potential and low-potential lines to the battery voltage UB, the faults F+0 and F−0 are shorts of these lines to the ground of the control apparatus, the fault F+− is a short circuit of both lines to each other, the faults F(+) and F(−) are interruptions of one of the two above-mentioned lines, respectively, the fault F(+)0 is a combination of faults F+0 and F(+) for the high-potential line, and the fault F(−)0 is a combination of the faults F−0 and F(−) for the low-potential line.

Figure 5:
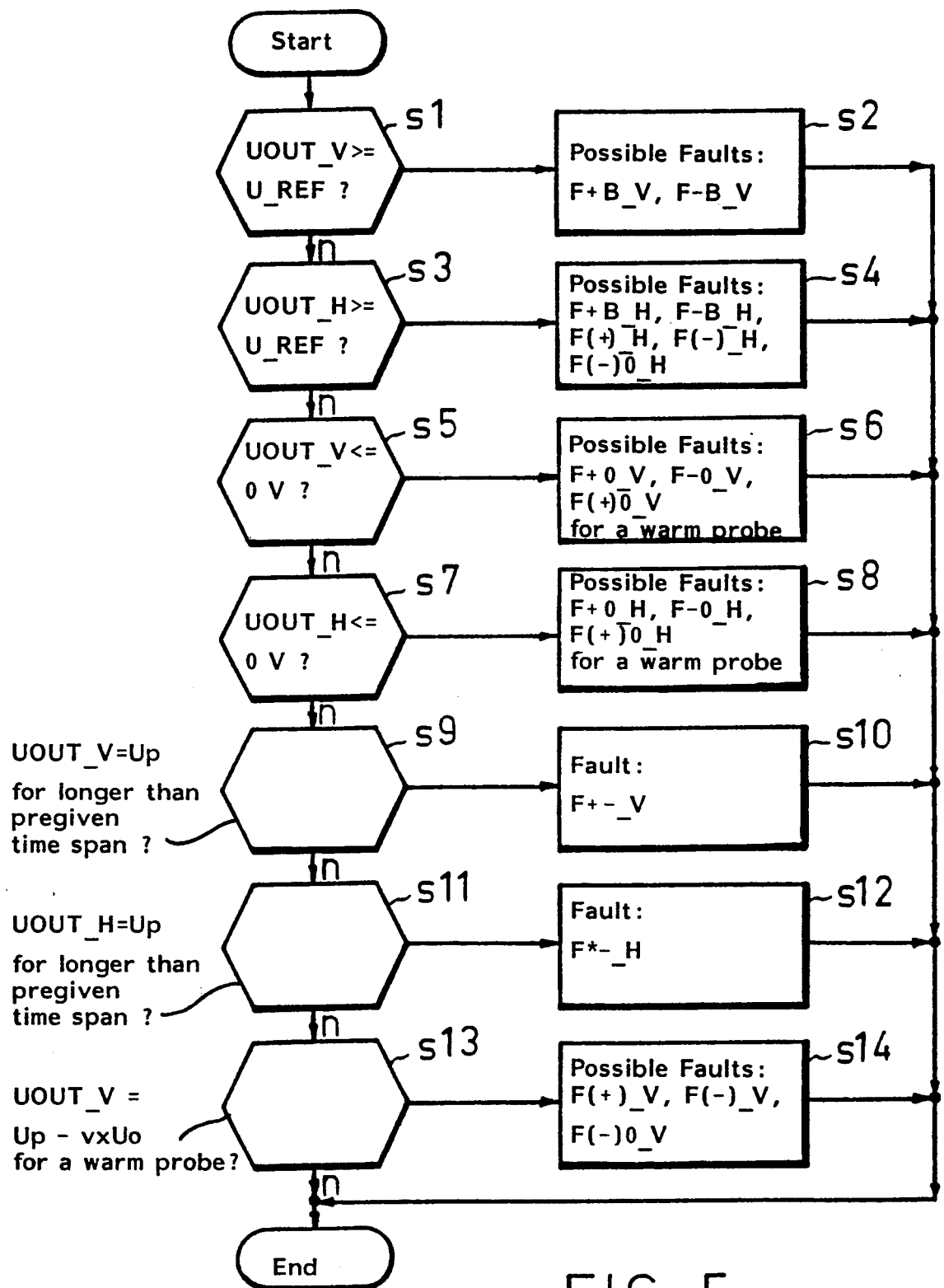

A method for determining defective probe connections is described with respect to the flowchart of FIG. 5. After the start of this method, a check is made (step s1) as to whether the output voltage UOUT_V of the forward amplifier corresponds at least to the reference voltage U_REF. This can then be the case when one of the two connecting lines is short circuited to battery voltage, that is, when there is one of the faults F+B_V or F−B_V. If in step s1 it is shown that the above-mentioned condition is fulfilled, then, in a step s2, an indication is provided that one of the above-mentioned faults is present.

If it develops in step s1 that the fault interrogated there is not present, a corresponding check follows in step s3 for the signal of the rearward probe. If the condition is fulfilled, then, in a corresponding manner, the faults F−B_H or F+B_H are present; however, the faults F(+)_H, F(−)_H and F(+)0_H are also possible. The corresponding fault indication, if required, follows in a step s4.

If the condition of step s3 is not satisfied, a check is made in a step s5 as to whether the output voltage UOUT_V is 0 V. This is possible for the faults F+0_V, F−0_V and F(−)0_V. For the fault F+0_V, that is the short circuit of the high-potential line HPL_V of the forward probe to the ground of the control apparatus, the possibility exists that for probes having negative probe voltage when measuring a gas having an air ratio greater than one, the voltage defined according to equation (1) of FIG. 1 temporarily becomes negative and, accordingly, the voltage of equation (2) (wherein the term Up is zero because of the ground short) becomes positive. A value of the output voltage UOUT_V different from zero will not remain continuously for a lambda control to approximately the air ratio one so that at least temporarily the unplausible value 0 V will occur which then immediately triggers the fault announcement according to step s6.

If none of the faults checked in step s5 is present, then a check is made in a step s7 as to whether the output voltage UOUT_H has the value 0 V. This is possible for the faults F+0_H, F−0_H and F(−)0_H. For the fault F+0_H, the same applies as explained for the fault F+0_V. If another fault is determined, then the indication takes place in a step s8.

With a no response to the inquiry in step s7, a step s9 follows wherein a check is made as to whether the output voltage UOUT_V is at the offset voltage Up for longer than a pregiven time span. This voltage is present continuously for the fault F+−_V; however, this voltage can also occur temporarily during proper operation. For each lambda control, the measured values fluctuate with a time-dependent period of very few seconds. For proper operation, the output voltage UOUT_V can therefore not be maintained longer than at most a few seconds at the value Up. The time span in the check of step s9 is correspondingly pregiven. If the time span exceeds the set time span with an output voltage of value Up which is continuously present, the fault F+−_V is indicated in step s10.

If the fault checked in step s9 is not present, then a corresponding check is made in a follow-on step s11 as to whether the output voltage UOUT_H has been present at the value Up for longer than a pregiven time span. This check for the rearward probe and a possible fault indication (fault F+−_H) in a step s10 take place in a manner corresponding to that described for the steps s9 and s10 for the forward probe.

If no condition checked up until now has been satisfied, then, finally, a check is made is a step s13 as to whether the output voltage UOUT_V is at the value Up−v·Uo when the forward probe SV is at operating temperature (warm probe). This voltage occurs for interruptions, namely, one of the faults F(+)_V, F(−)_V or F(+)0_V since then the internal resistance RS_V of the probe appears to be infinite because of the interruption and therefore, the second summation term in equation (1) of FIG. 1 is zero. However, the voltage can also occur for a cold probe and therefore a high internal resistance RS_V. For this reason, the additional condition of an operationally warm probe is interrogated in step s13. Adequate operational warmth then can be checked in accordance with any known type, for example, by monitoring a specific time-dependent trace of the probe signal or by measuring the internal resistance of the probe. If the conditions of step s13 are satisfied, then, in step s14, an indication is provided that one of the faults FV, GV or IV is present. Otherwise, the end of the method is reached.

The fault indications in the above-mentioned even numbered steps can then simply be that a corresponding announcement is read into a fault memory; however, it is more advantageous to emit an acoustic or optical warning indication since faults, especially in connection with the forward probe, are very critical for the discharge of toxic gas. With the occurrence of connecting faults of the forward probe, it is mostly necessary to switch over from a lambda closed-loop control to a lambda open-loop control. In the case of a connection failure of the rearward probe, it is in contrast mostly not necessary to switch over to a lambda open-loop control; instead, a fine matching method for the control is simply dropped. The foregoing notwithstanding, it is recommended to display the nonoccurrence of the signals of the rearward probe. A display can also take place after an attempt to correct the fault is unsuccessful. Details of the fault display are however of no significance with respect to the invention.

It is understood that the foregoing description is that of the preferred embodiments of the invention and that various changes and modifications may be made thereto without departing from the spirit and scope of the invention as defined in the appended claims.

What is claimed is:

1. A connecting circuit for a potential-free oxygen probe having a low-potential line and a high-potential line, the connecting circuit comprising:

an amplifier;

an offset voltage source connected to said high-potential line forward of said amplifier for applying an offset potential to said high-potential line;

said amplifier having an input connected across said high-potential and low-potential lines to receive the difference between the potentials on said lines as an input voltage;

said amplifier being adapted to amplify said input voltage and having an output for supplying an output voltage equal to the difference between said offset voltage and the amplified input voltage; and, said offset voltage being selected so as to cause said output voltage to always be greater than zero but less than a pregiven threshold voltage.

2. The connecting circuit of claim 1, further comprising an analog/digital converter having a reference voltage; and, said threshold voltage being equal to said reference voltage.

3. The connecting circuit of claim 1, further comprising a pull-up resistor connecting said low-potential line to said threshold voltage.

4. The connecting circuit of claim 1, wherein said oxygen probe has a resistance having a first resistance value when said oxygen probe is cold and a second resistance value when said oxygen probe is warm; and, wherein said connecting circuit further comprises a series circuit connected in parallel with said oxygen probe; said series circuit including an ancillary voltage source and a resistor; and, said resistor having a resistance value less than said first resistance value but greater than said second resistance value.

5. The connecting circuit of claim 1, said oxygen probe being a first oxygen probe and said connecting circuit being simultaneously provided for a second oxygen probe having a low-potential line and a high-potential line connected to said low-potential line and said high-potential line, respectively, of said first oxygen probe.

6. A method for checking the correct connection of a potential-free oxygen probe having a low-potential line and a high-potential line, the method comprising the steps of:

raising the potential on said high-potential line relative to ground by a pregiven offset voltage;

applying the difference of the potentials on said lines to an amplifier as an input voltage;

amplifying said input voltage and subtracting the amplified input voltage from said offset voltage to form a difference voltage as the output voltage of said amplifier;

deeming said probe to be improperly connected when said output voltage is at most zero or corresponds at least to a pregiven threshold voltage; and, selecting said offset voltage so as to cause said output voltage to be always greater than zero and less than said pregiven threshold voltage when said oxygen probe is correctly connected.

7. The method of claim 6, the oxygen probe emitting an output voltage and the method comprising the further steps of:

applying the output voltage of said oxygen probe as an analog voltage to an analog/digital converter and applying said threshold voltage to said analog/digital converter as a reference voltage;

checking to determine if said analog/digital converter indicates the presence of at least said reference voltage as an analog voltage; and, then, if this is the case, concluding that there is a short circuit of one of said lines of said oxygen probe to the high potential of a vehicle battery.

8. The method of claim 6, further comprising the steps of:

checking to determine if the output voltage of the probe has the value zero; and, if so, concluding that there is a short circuit of one of said lines to ground.

9. The method of claim 6, wherein said probe operates on a two-level lambda control and emits an output voltage, the method further comprising the steps of:

checking to determine if the output voltage of the oxygen probe remains at said offset voltage for longer than a pregiven time span; and, if so, concluding that both of said lines are short circuited to each other.

* * * * *